(12) United States Patent
Askill et al.

(10) Patent No.: US 6,328,910 B1
(45) Date of Patent: Dec. 11, 2001

(54) CYANOACRYLATE COMPOSITIONS COMPRISING AN INDICATOR

(75) Inventors: Ian N. Askill, Colorado Springs, CO (US); Richard J. Greff, St. Pete Beach, FL (US)

(73) Assignee: MedLogic Global Corporation, Colorado Springs, CO (US)

( * ) Notice: Subject to any disclaimer, the term of this patent is extended or adjusted under 35 U.S.C. 154(b) by 0 days.

(21) Appl. No.: 09/370,670

(22) Filed: Aug. 9, 1999

Related U.S. Application Data

(60) Provisional application No. 60/095,686, filed on Aug. 7, 1998.

(51) Int. Cl.[7] .......................... C09K 19/36; C09K 19/38; G01K 11/18; A61B 5/01
(52) U.S. Cl. .................. 252/299.7; 252/299.01; 252/299.5; 374/162; 600/549
(58) Field of Search .......................... 374/162; 345/106; 252/299.01, 299.7, 299.5; 514/527; 600/549

(56) References Cited

U.S. PATENT DOCUMENTS

| 5,684,042 | * | 11/1997 | Greff et al. | 514/527 |
| 5,753,699 | * | 5/1998 | Greff et al. | 514/527 |

FOREIGN PATENT DOCUMENTS

2074975 * 11/1981 (GB) .

* cited by examiner

*Primary Examiner*—Shean C. Wu
(74) *Attorney, Agent, or Firm*—Burns, Doane, Swecker & Mathis LLP

(57) ABSTRACT

Disclosed are cyanoacrylate compositions comprising a cyanoacrylate prepolymer and an encapsulated temperature sensitive indicator. These compositions provide for in situ formation of an polymeric cyanoacrylate film on mammalian skin which can be used to monitor the surface skin temperature of the mammal.

43 Claims, No Drawings

CYANOACRYLATE COMPOSITIONS COMPRISING AN INDICATOR

This application claims benefit to provisional application No. 60/095,686 filed Aug. 7, 1998.

BACKGROUND OF THE INVENTION

Field of the Invention

This invention is directed to cyanoacrylate prepolymer compositions comprising encapsulated temperature sensitive indicators. These compositions provide for in situ formation of polymeric cyanoacrylate films on mammalian skin which films are useful for monitoring the temperature, temperature differentials and temperature patterns of mammalian skin.

This invention is also directed to methods and kits for monitoring mammalian skin temperature by use of such compositions.

REFERENCES

The following publications, patent applications and patents are cited in this application as superscript numbers:

1. Hawkins, et al., Surgical Adhesive Compositions, U.S. Pat. No. 3,591,676, issued Jul. 6, 1971
2. Halpen, et al., Adhesive for Living Tissue, U.S. Pat. No. 3,667,472, issued Jun. 6, 1972
3. McIntire, et al., Process for the Preparation of Poly(α-Cyanoacrylates), U.S. Pat. No. 3,654,239, issued Apr. 4, 1972
4. Leplyanin, Medical and Surgical Adhesive Composition and Process for Its Preparation, International Application Publication No. WO 96123532 published Aug. 8, 1996
5. Bolduc, "Aerosol Spray System", U.S. Pat. No. 5,154,320, issued Oct. 13, 1992
6. Otake, et al., U.S. Pat. No. 4,183,684
7. Rabinowitz, et al., Method of Surgically Bonding Tissue Together, U.S. Pat. No. 3,527,224, issued Sep. 8, 1970
8. Kronenthal, et al., Surgical Adhesives, U.S. Pat. No. 3,995,641, issued Dec. 7, 1976
9. Davydov, et al., Medical Adhesive, U.S. Pat. No. 4,035,334, issued Jul. 12, 1977
10. Waniczek, et al., Stabilized Cyanoacrylate Adhesives Containing Bis-Trialkylsilyl Esters of Sulfuric Acid, U.S. Pat. No. 4,650,826, issued Mar. 17, 1987
11. Greff, et al., Cyanoacrylate Compositions Comprising an Antimicrobial Agent, U.S. Pat. No. 5,684,042 on Nov. 4, 1997.
12. Greff, et al., Prepolymer Compositions Comprising an Antimicrobial Agent, U.S. patent application Ser. No. 08/963,236 filed on Nov. 3, 1997
13. Suzuki, et al., Cholesteric Liquid Crystalline Phase Material-Dye Composition and Venipuncture Method Employing the Composition, U.S. Pat. No. 4,015,591, issued Apr. 5, 1977
14. Suzuki, et al., Venipuncture Method, U.S. Pat. No. 4,175,543, issued Nov. 27, 1979
15. Goldberg, et al., Temperature Sensing Means and Methods, U.S. Pat. No. 3,533,399, issued Oct. 13, 1970
16. O'Sullivan, et al., High Viscosity Cyanoacrylate Adhesive Compositions, and Process for Their Preparation, U.S. Pat. No. 4,038,345, issued Jul. 26, 1977
17. Woodsmansee, Liquid Crystal Compositions, U.S. Pat. No. 3,441,513, issued Apr. 29, 1969
18. Fergason, et al., Thermal Imaging Devices Utilizing a Cholesteric Liquid Crystalline Phase Material, U.S. Pat. No. 3,114,836, issued Dec. 17, 1963
19. Joyner, et al., Plasticized Monomeric Adhesive Compositions and Articles Prepared Therefrom, U.S. Pat. Nos. 2,784,127, issued Mar. 5, 1957
20. Columbus, et al., Adhesive Cyanoacrylate Compositions with Reduced Adhesion to Skin, U.S. Pat. No. 4,444,933, issued Apr. 24, 1984
21. Lee, et al., U.S. patent application Ser. No. 08/962,868 "Kits Containing Cyanoacrylate Compositions Comprising an Antimicrobial Agent" filed Nov. 3, 1997
22. Askill, et al., U.S. patent application Ser. No. 09/062,514, for "Package for Cyanoacrylate Composition" filed Apr. 17, 1998

All of the above publications, patent applications and patents are herein incorporated by reference in their entirety to the same extent as if each individual publication, patent application or patent was specifically and individually indicated to be incorporated by reference in its entirety.

State of the Art

Conventional skin temperature monitors, such as adhesive strips with temperature sensitive panels, have been used to monitor human surface body temperatures. In particular, commercially available adhesive strips have an adhesive backing on one side of the strip and are placed, e.g., on the forehead of a human patient to monitor the presence of fever, instead of using a standard thermometer which can be awkward for infants and children. These strips are also helpful for use in patients who cannot effectively communicate with the care giver, such as comatose patients or patients recovering from surgery. The use of the monitoring strip is generally limited to a short one-time use, after which the strip is removed and disposed. Thus, the temporary nature of these strips requires that a new strip be applied each time that the temperature needs to be monitored.

The use of these strips is typically limited to areas of the skin which are generally flat and free of hair and, accordingly, are used for the most part in monitoring the skin temperature of the patient. There are, however, numerous situations where localized temperature differentials on adjacent skin surfaces are indicative of incipient disease conditions or other conditions. Such localized temperature differentials include "hot spots" on mammalian skin surface associated with, for example, incipient diabetic ulcer formation, incipient wound infection, etc. Further, such localized temperature differentials could be used with monitor "cold spots" such as those produced by skin grafts, tissue flaps, frost-bite, etc.

The evaluation of the presence and location of such skin surface "hot spots" is critical for early intervention against the incipient condition associated with the hot spot. Prior art strips are impractical for such an evaluation because of the limited environment where such strips can be used. For example, these strips cannot be used over scabs, wounds or other infected areas. Nor are these strips useful in veterinary medicine since they do not adhere well to the skin of animals such as horses, dogs and cats. Moreover, even if these strips were applied to the animal, any irritation caused to the animal by these strips would invariably cause the animal to remove the strip (e.g., by scratching). Accordingly, a temperature monitoring composition capable of placement over any mammalian skin surface in the presence or absence of hair would be particularly beneficial.

This invention contemplates that temperature monitoring components such as encapsulated cholesteric liquid crystals are compatible with and can be included in cyanoacrylate ester prepolymer compositions which compositions can then be polymerized in situ on any contour of mammalian skin, in the presence or absence of hair, to provide an adhesive polymeric layer containing a temperature sensitive component which can monitor the underlying mammalian skin temperature.

Cholesteric liquid crystalline phase materials, also referred to as cholesteric liquid crystals ("liquid crystals"), have unusually high thermal sensitivity. These materials are a class of compounds that display cholesteric mesophase within certain temperature limits. The cholesteric mesophase is a state of matter intermediate in molecular ordering between a crystalline solid and an isotropic liquid. In general, the materials are colorless in their solid and isotropic liquid states, assuming the coloration of their background or of light-absorptive materials added thereto. When liquid crystals are in the cholesteric mesophase, and ordinary white light is directed at the material, the light is separated essentially into two components, one of which is transmitted and one of which is scattered or reflected. The scattered light gives the material an iridescent color, which depends upon the material, the temperature, and the angle of the incident light beam, i.e., the liquid crystals demonstrate color-temperature sensitivity when in the cholesteric phase. Minute changes, as small as 0.1° C., in skin temperatures are readily discerned by significant changes in color of the particular area under observation. Thus, a change in temperature results in a change in color that can be easily monitored.

The liquid crystals are typically provided in encapsulated form and the use of such encapsulated liquid crystals to monitor temperature is well-known in the art. For example, Goldberg, et al.[15] apply compositions containing liquid crystals to skin that have previously been covered with polyvinyl alcohol film to measure temperature. Also, Suzuki, et al.[14] apply liquid crystals in the form of a paste to precooled skin to delineate a vein for venipuncture.

Many efforts have been made to incorporate liquid crystals into polymeric sheets which are then applied to the skin. These sheets do not have a high resolution for detecting small temperature differences because of the high heat capacities of the polymers. Moreover, such polymeric sheets, by themselves, typically do not adhere well to the skin and leave air pockets between the skin and the film surface.

The incorporation of encapsulated temperature sensitive compounds directly into a prepolymeric composition for subsequent application and in situ polymerization on mammalian skin is apparently not known in the art. Such prepolymers, such as cyanoacrylate esters, do not possess the ability either in the prepolymer or polymer phase to indicate temperature. Accordingly, such temperature sensitive compositions require the incorporation of temperature sensitive indicators into the prepolymeric composition and that sufficient amounts of this indicator be present in the polymeric film to monitor the temperature of the skin area on the mammal.

The incorporation of such an encapsulated temperature sensitive indicator into the prepolymer composition is problematic at best because several disparate criteria must be simultaneously met. First, the encapsulated temperature sensitive indicator must be dispersible in the prepolymer composition at the concentrations necessary to effect the monitoring of the mammal's skin temperature. Second, the encapsulated temperature sensitive indicator employed must not cause premature polymerization of the prepolymer. Third, the encapsulated temperature sensitive indicator employed must not prevent in situ polymerization of the prepolymer when applied to the skin. Fourth, the encapsulated temperature sensitive indicator must be compatible with the intended use of the polymeric film by not inhibiting formation of a flexible, durable film. Fifth, the polymeric film must not interfere with the temperature sensitive indicator's ability to detect changes in temperature.

In view of the clear benefits associated with the incorporation of a temperature-sensitive indicator directly into a prepolymer composition, there is an ongoing need to formulate a prepolymer composition comprising a temperature sensitive material for monitoring the skin temperature of a mammal.

SUMMARY OF THE INVENTION

This invention is directed to cyanoacrylate ester compositions comprising an effective amount of an encapsulated temperature-sensitive agent to monitor, for example, the surface skin temperature of a mammal. These compositions provide for in situ formation of an adherent temperature-sensitive polymeric cyanoacrylate film on mammalian skin where the surface skin temperature or temperature pattern of the mammal can be determined typically by the color of the film.

Accordingly, in one of its composition aspects, this invention is directed to a cyanoacrylate composition which comprises:

(a) a polymerizable cyanoacrylate ester; and
(b) an effective amount of an encapsulated temperature-sensitive indicator.

Preferably, the polymerizable cyanoacrylate ester is a polymerizable monomer or reactive oligomer of a cyanoacrylate ester. Such monomers and reactive oligomers are sometimes referred to herein simply as "prepolymers" and, in monomeric form, are preferably represented by formula I:

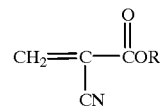

wherein R is selected from the group consisting of alkyl, alkenyl, cycloalkyl, aryl, alkalkoxy, and a substituent of the formula:

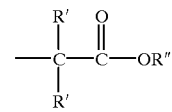

wherein each R' is independently selected from the group consisting of. hydrogen and methyl, and R" is selected from the group consisting of. alkyl, alkenyl, alkynyl, cycloalkyl, aralkyl, aryl, and substituted aryl.

More preferably, in the cyanoacrylate esters of formula I, R is alkyl of from 2 to 10 carbon atoms and still more preferably alkyl of from 4 to 8 carbon atoms. Even more preferably, R is butyl, octyl or decyl and most preferably, R is n-butyl.

In a preferred embodiment the cyanoacrylate composition comprises:

(a) a polymerizable cyanoacrylate ester which, in monomeric form, is represented by formula II:

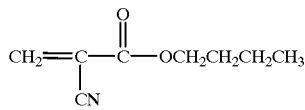

(b) an effective amount of an encapsulated temperature-sensitive indicator.

The temperature sensitive agents preferably are encapsulated enantiotropic cholesteric liquid crystalline phase materials or liquid crystals. Preferably two, three or four-component liquid crystal compositions are employed, for providing a desired color response and a mesophase or color-display temperature range at a desired temperature level and having a suitable width of temperature range. Preferably, the liquid crystals are selected to provide a color response in the mesophase range changing with increasing temperature from red through orange, yellow, green and blue to violet in the visible spectrum, as a result of light scattering by the liquid crystals.

The cyanoacrylate compositions can optionally further comprise a polymerization inhibitor and/or a biocompatible plasticizer. Preferred polymerization inhibitors are sulfur dioxide and/or 4-methoxyphenol which are preferably employed at from about 50 to about 500 ppm, and preferably at from about 200 to about 500 ppm, based on the total weight of the composition. The preferred biocompatible plasticizer is dioctyl phthalate or tributyl acetyl citrate which is preferably employed at from about 18 to 25 weight percent based on the total weight of the composition. In a preferred embodiment, the compositions can further comprise an effective amount of an antimicrobial agent.

In one of its method aspects, this invention is directed to a method of monitoring the temperature of a mammal which comprises:

applying to at least a portion of the skin surface of said mammal a sufficient amount of a cyanoacrylate composition comprising a polymerizable cyanoacrylate ester and an effective amount of an encapsulated temperature-sensitive indicator which indicates the temperature of the skin surface so as to cover the entire desired surface by providing a unique color for a particular temperature;

polymerizing the cyanoacrylate composition so as to form a polymeric film which adheres to the surface where the composition was applied; and monitoring the temperature of said mammal by correlating the color of the temperature-sensitive indicator to the particular temperature.

In another of its method aspects, this invention is directed to a method of determining temperature differentials on adjacent skin surfaces of a mammal which comprises:

applying to said adjacent skin surfaces of said mammal a sufficient amount of a cyanoacrylate composition comprising a polymerizable cyanoacrylate ester and an effective amount of an encapsulated temperature-sensitive indicator, which indicates the temperature of the skin surface, so as to cover the entire surfaces;

polymerizing the cyanoacrylate composition so as to form a polymeric film which adheres to the area where the composition was applied; and determining any temperature differentials between the adjacent skin surfaces by monitoring the colors emitted by the temperature-sensitive indicator on said adjacent skin surfaces.

This method is particularly useful in determining temperature differentials on adjacent skin associated with incipient disease conditions such as decubitis ulcer formation, diabetic ulcer formation and the like. Nevertheless, this method can also be used to evaluate temperature differentials on adjacent skin associated with skin grafts or skin flaps to evaluate the condition of the graft or flap.

This invention is also directed to kits useful for applying the cyanoacrylate compositions described herein onto mammalian skin. In particular, such a kit of parts comprises (a) a container comprising therein a prepolymeric composition which, in turn, comprises a polymerizable cyanoacrylate ester and an encapsulated temperature-sensitive indicator; and (b) an applicator means for applying the composition onto mammalian skin.

In another of its kit aspects, this invention is also directed to kits useful for applying the cyanoacrylate compositions described herein onto mammalian skin. In particular, such a kit of parts comprises (a) a container comprising therein a polymerizable cyanoacrylate ester; (b) a container comprising an encapsulated temperature-sensitive indicator; and (c) an applicator means for applying the composition onto mammalian skin.

Preferably, in such kits, the amount of encapsulated temperature-sensitive indicator included therewith is sufficient to allow unaided visual detection of the color emitted by the indicator. More preferably, the encapsulated temperature-sensitive indicator is employed in a range of from about 5 to 40 weight percent based on the total weight of the composition.

DETAILED DESCRIPTION OF THE PREFERRED EMBODIMENTS

This invention is directed, in part, to cyanoacrylate compositions comprising a temperature sensitive indicator. However, prior to discussing this invention in further detail, the following terms will first be defined.

Definitions

As used herein, the following terms have the following meanings:

The term "cyanoacrylate ester compositions" or "cyanoacrylate compositions" refers to polymerizable formulations comprising polymerizable cyanoacrylate ester monomers and/or oligomers which, in their monomeric form, are preferably compounds represented by formula I as described above.

More preferably, in formula I, R is an alkyl group of from 2 to 10 carbon atoms including, by way of example, ethyl, n-propyl, iso-propyl, n-butyl, iso-butyl, sec-butyl, n-pentyl, iso-pentyl, n-hexyl, iso-hexyl, 2-ethylhexyl, n-heptyl, n-octyl, nonyl, and decyl. More preferably, R is butyl, octyl or decyl and most preferably, R is n-butyl. Mixtures of such compounds can also be employed.

Polymerizable cyanoacrylate esters are known in the art and are described in, for example, U.S. Pat. Nos. 3,527,224; 3,591,676; 3,667,472; 3,995,641; 4,035,334; and 4,650,826.[1,2,7–10] The disclosures of each are incorporated herein by reference in their entirety.

A particularly preferred cyanoacrylate ester for use in the invention is n-butyl-2-cyanoacrylate.

The polymerizable cyanoacrylate ester compositions described herein rapidly polymerize in the presence of water vapor or tissue protein, and the n-butyl-cyanoacrylate bonds human skin tissue without causing histotoxicity or cytotoxicity.

Such polymerizable cyanoacrylate esters are sometimes referred to herein as prepolymers and compositions comprising such esters are sometimes referred to herein as prepolymer compositions.

"Alkyl" refers to monovalent alkyl groups preferably having from 1 to 10 carbon atoms and more preferably 2 to 10 carbon atoms. This term is exemplified by groups such as methyl, ethyl, n-propyl, iso-propyl, n-butyl, iso-butyl, n-hexyl, and the like "Alkylene" refers to divalent alkylene groups preferably having from 1 to 10 carbon atoms and more preferably 1 to 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Aralkyl" refers to -alkylene-aryl groups preferably having from 1 to 10 carbon atoms in the alkylene moiety and from 6 to 10 carbon atoms in the aryl moiety. Such alkaryl groups are exemplified by benzyl, phenethyl and the like.

"Alkoxy" refers to the group "alkyl-O—" where alkyl is as defined herein. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkalkoxy" refers to the group "-alkylene-O-alkyl" where alkylene and alkyl are as defined above. Such groups include, by way of example, methylenemethoxy (—$CH_2OCH_3$), ethylenemethoxy (—$CH_2CH_2OCH_3$), n-propylene-iso-propoxy (—$CH_2CH_2CH_2OCH(CH_3)_2$), methylene-tert-butoxy (—$CH_2$—O—$C(CH_3)_3$) and the like.

"Alkenyl" refers to monovalent alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH═$CH_2$), n-propenyl (—$CH_2$CH═$CH_2$), iso-propenyl (—$C(CH_3)$═$CH_2$), and the like.

"Alkynyl" refers to monovalent alkynyl groups preferably having from 2 to 10 carbon atoms and more preferably 2 to 6 carbon atoms and having at least 1 and preferably from 1–2 sites of alkynyl unsaturation. Preferred alkynyl groups include ethynyl (—C≡CH), propargyl (—$CH_2$C≡CH) and the like. "Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

"Substituted aryl" refers to aryl groups substituted with from 1 to 3 substituents selected from the group consisting of alkyl, alkoxy, hydroxyl, halo, nitro and aryl.

"Cycloalkyl" refers to cyclic alkyl groups of from 3 to 20 carbon atoms having a single cyclic ring or multiple condensed rings (including aromatic rings fused to the cycloalkyl ring) which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as dibenzosuberane, adamantanyl, and the like.

The term "compatible" as it relates to compatible encapsulated temperature sensitive indicators refers to materials that are compatible with in vivo applications of cyanoacrylate ester compositions onto mammalian skin including human skin. Compatibility is assessed using a number of criteria. First, the encapsulated temperature-sensitive indicator must be dispersible in the cyanoacrylate composition at the concentrations necessary to effect the monitoring of the mammal's temperature. Second, the encapsulated temperature sensitive indicator employed must not cause premature polymerization of the cyanoacrylate ester composition. Third, the encapsulated temperature-sensitive indicator employed must not prevent in situ polymerization of the cyanoacrylate composition when applied to the skin. Fourth, the encapsulated temperature-sensitive indicator must be compatible with the intended use of the polymeric film by not inhibiting formation of a flexible, durable film. Fifth, the polymeric film must not interfere with the encapsulated temperature-sensitive indicator's ability to detect changes in temperature. Sixth, the temperature-sensitive indicator must be compatible with topical application onto mammalian skin including compatibility measured by the lack of release of irritating or toxic substances onto/into the skin.

The term "temperature sensitive indicator" refers to agents that emit differential signals under varying thermal conditions. Preferably such signals are physically perceived signals, such as different colors at different temperatures, but other non-physically perceived signals (changes) can be used provided that such signals are detectable. For example, non-physically perceived signals include changes in UV or IR light emissions which can be detected by a UV or IR detector and transformed into a visible display. However, for ease of application and measurement, the temperature sensitive indicators preferably emit a change in visible color as the temperature is varied.

The term "encapsulated temperature sensitive indicator" refers to temperature sensitive indicators encapsulated within a thin film or surfactant which encapsulation separates the indicators from the cyanoacrylate prepolymer. Such encapsulated temperature sensitive indicators are well known in the art and include those commercially available from Cole-Parmer Instrument Company, Vernon Hills, Ill., USA.

Reference to an "enantiotropic" material means a liquid asymmetric crystal denoting asymmetric crystal forms (enantiomorphs) capable of existing in reversible equilibrium with each other which forms, or a mixture of liquid crystals which together form the cholesteric mesophase either by heating the material in its crystalline solid phase or by cooling the material in its isotropic liquid phase.

The term "cholesteric mesophase" refers to a state of matter intermediate in molecular ordering between a crystalline solid and an isotropic liquid.

Preferred agents would include the cholesteryl, dicholesteryl, cholestanyl, and sitosteryl organic esters, halides and alkyl carbonates. Table 1 is a list of liquid crystals, as previously disclosed in U.S. Pat. No. 4,015,591[13] which are further preferred in the invention. Other patents disclosing such compositions include Woodsmansee[17] and Fergason, et al.[18]

TABLE 1

| Compound name | Abbreviation |
| --- | --- |
| Cholesterol erucyl carbonate | CEC |
| Cholesterol methyl carbonate | GMC |
| Cholesterol oleyl carbonate | COC |
| Cholesterol para-nonyl phenyl carbonate | CNPC |
| Cholesterol phenyl carbonate | CPC |
| Cholesterol acetate | CA |
| Cholesterol benzoate | Cbz |
| Cholesterol butyrate | CB |
| Cholesterol isobutyrate | CiB |
| Cholesterol chloride | Ccl |
| Cholesterol chloroacetate | CCA |
| Cholesterol cinnamate | Ccn |
| Cholesterol crotanoate | Ccr |
| Cholesterol decanoate | Cdc |
| Cholesterol erucate | CE |

TABLE 1-continued

| Compound name | Abbreviation |
| --- | --- |
| Cholesterol heptanoate | Chp |
| Cholesterol hexanoate | Chx |
| Cholesterol myristate | Cmy |
| Cholesterol nonanoate | CN |
| Cholesterol octanoate | Cot |
| Cholesterol oleate | CO |
| Cholesterol propionate | CP |
| Cholesterol valerate | CV |
| Dichloresteryl Carbonate | DCC |
| Cholestanyl Benzoate | CaBz |
| Sitosteryl nonanoate | SN |

Preferred liquid crystal compositions and their mesophase temperature ranges are listed in Table 2.

TABLE 2

| No. | Components of Composition in % by weight | | | | Mesophase temperature range, °C. |
| --- | --- | --- | --- | --- | --- |
| 1 | 52% CN | 32% COC | 7% Cbz | 9% DCC | 31–34 |
| 2 | 60% CN | 25% COC | 15% Cbz | | 30–37 |
| 3 | 56% CN | 35% COC | 9% Cbz | | 32–35 |
| 4 | 75% CN | 9% COC | 16% Cbz | | 29–37 |
| 5 | 75% CN | 10% COC | 15% Cbz | | 30–38 |
| 6 | 78% CN | 5% COC | 17% Cbz | | 34–37 |
| 7 | 85% CN | 5% COC | 10% Cbz | | 30–36 |
| 8 | 50% CN | 26% COC | 14% Cbz | 10% CNPC | 29–33 |
| 9 | 50% CN | 33% COC | 8% Cbz | 9% DC | 28–33 |
| 10 | 56% CN | 44% COC | | | 31–32 |
| 11 | 48% CN | 44% COC | 8% CBz | | 31–33 |
| 12 | 47% CN | 43% COC | 7% CBz | 3% CCI | 30–33 |
| 13 | 23% CN | 60% COC | 17% Cbz | | 29–31 |
| 14 | 70% CEC | 15% COC | 15% Cbz | | 28–30 |
| 15 | 40% CN | 40% COC | 5% Cbz | 15% CaBz | 30–34 |
| 16 | 5% CN | 80% COC | 6% Cbz | 15% CaBz | 33–36 |
| 17 | 51% CN | 35% COC | 8% Cbz | 6% DCC | 30–33 |
| 18 | 48% CN | 40% COC | 4% Cbz | 8% DCC | 29–32 |
| 19 | 64% CN | 27% COC | 2% Cbz | 7% CMC | 27–33 |
| 20 | 57% CN | 38% COC | 5% Cbz | | 29–32 |
| 21 | 59% CN | 35% COC | 3% Cbz | 3% CA | 30–33 |
| 22 | 38% CN | 51% COC | 5% Cbz | 6% DCC | 27–30 |
| 23 | 37% CN | 50% COC | 7% Cbz | 6% DCC | 25–28 |

Other encapsulated temperature sensitive indicators include those having temperature sensitivity from 35° to 40° C. and 40° C. to 45° C. and are commercially available from Cole-Parmer Instrument Company, Vernon Hills, Ill., USA.

With regard to the above, it is well known that mammalian skin temperature varies over the surface of the mammalian body. For example, human surface skin temperatures generally range from about 28° C., to 37° C., in venous areas, and may go down to 21° C., or up to 39° C. For example, skin temperatures in the antecubital fossa and upper forearm are about 30–32° C. while in the lower extremities skin temperature can be about 28° C.

The compositions described above, accordingly, provide great selectivity is selecting the appropriate composition for measuring temperatures over the relevant skin surface.

The term "biocompatible plasticizer" refers to any material which is soluble or dispersible in the cyanoacrylate composition, which increases the flexibility of the resulting polymer film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127[19] and 4,444,933[20] the disclosures of both of which are incorporated herein by reference in their entirety. Specific plasticizers include, by way of example only, acetyl tri-n-butyl citrate (preferably ~20 weight percent or less), acetyl trihexyl citrate (preferably ~20 weight percent or less) butyl benzyl phthalate, dibutyl phthalate, dioctylphthalate, n-butyryl tri-n-hexyl citrate, diethylene glycol dibenzoate (preferably ~20 weight percent or less) and the like. The particular biocompatible plasticizer employed is not critical and preferred plasticizers include dioctylphthalate and acetyl tri-n-butyl citrate.

The term "polymerization inhibitor" refers to conventional inhibitors of cyanoacrylate esters including materials such as sulfur dioxide, 4-methoxyphenol, glacial acetic acid, and the like. The polymerization inhibitor is typically employed in amounts effective to inhibit polymerization until application onto the mammalian skin. Because of its compatibility with topical skin applications, the polymerization inhibitor is preferably sulfur dioxide. Other preferred polymerization inhibitors include glacial acetic acid, free radical inhibitors (e.g., hydroquinones) and the like and mixtures thereof (e.g., mixtures of glacial acetic acid and 4-methoxyphenol).

The term "antimicrobial agent" refers to agents which interact with microbes (i.e., bacteria, fungi, viruses and microbial spores) thereby preventing their development and pathogenic action. Examples of antimicrobial agents include polyvinylpyrrolidone iodine complexes (PVP-$I_2$). Preferably, the antimicrobial agent does not interact with the cyanoacrylate causing premature polymerization of the pre-polymeric cyanoacrylate.

The term "temperature" refers not only to temperature as used conventionally, but also to temperature differentials and temperature patterns (e.g., the change in temperature over a relatively small section of skin surface).

Compositions

This invention is directed to compositions comprising an encapsulated temperature sensitive indicator and cyanoacrylate esters forming a prepolymer composition which, upon polymerization, provides for a cyanoacrylate polymeric film useful in monitoring mammalian surface skin temperatures. Compatibility can be assessed by the fact that these encapsulated indicators are expected to be dispersible in the cyanoacrylate ester composition at effective concentrations and when so employed, will not cause premature polymerization of the cyanoacrylate ester composition and will not prevent effective polymerization of the cyanoacrylate ester composition when applied to mammalian skin. Further, the polymeric film will not interfere with the temperature sensitive agent's ability to respond to temperature differentials. Moreover, the polymerizable cyanoacrylate ester composition comprising such indicators will form a flexible, durable polymeric film having the encapsulated indicator incorporated therein which indicator allows monitoring of the temperature of a mammal. Lastly, the indicator employed will not cause moderate to severe skin irritation and will not be toxic.

The compositions of this invention are prepared by adding a sufficient amount of the encapsulated temperature-sensitive indicator to the cyanoacrylate ester composition in order to monitor temperature on mammalian skin when this composition polymerizes therein to form a cyanoacrylate polymer film. The encapsulated indicators are preferably added as a solid composition. In this regard, the use of organic solvents may cause premature polymerization of the cyanoacrylate ester and may also interfere with the indicator's mesophase properties, altering their optical effects. Accordingly, the compositions described herein are preferably free of added solvents (e.g., organic solvents such as chloroform, methanol, ethanol, toluene, ethyl acetate, hexane, etc.).

The composition of the temperature-sensitive indicators and the cyanoacrylate ester can be formulated to a specific viscosity to meet disparate demands for the intended application of the composition. For example, relatively low viscosities are often preferred where application is to be made to a large surface area (e.g., an abdomen). This preference results from the fact that these forms are less viscous and, accordingly, will permit more facile large surface area application of a thin film. Contrarily, where application is to be made to a specific position on the skin (e.g., elbow surfaces, knee surfaces and the like), higher viscosity compositions, including those containing thixotropic materials, are preferred to prevent "running" of the compositions to unintended locations.

Accordingly, these compositions have a viscosity of from about 2 to 50,000 centipoise at 20° C. For low viscosity applications, viscosity ranges of from about 2 to 1,500 centipoise at 20° C. are preferred. More preferably, the cyanoacrylate ester employed in the composition is almost entirely in monomeric form and the composition has a viscosity of from about 5 to about 500 centipoise at 20° C.

A thickening agent is optionally employed to increase the viscosity of the composition which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like, with PMMA being preferred. Fumed silica is particularly useful in producing a gel for topical application having a viscosity of from about 1500 to 50,000. Suitable thickening agents for the cyanoacrylate compositions described herein also include a polymer of the alkyl cyanoacrylate as disclosed in U.S. Pat. Nos. 3,654,239[3] and 4,038,345[16] both of which are incorporated herein by reference in their entirety.

Thickening agents are deemed to be biocompatible if they are soluble or dispersible in the composition and are compatible with the skin as measured by the lack of moderate to severe skin irritation.

The cyanoacrylate composition preferably includes a biocompatible plasticizer and such plasticizers are preferably included from about 10 to 30 weight percent and more preferably from about 18 to 25 weight percent based on the weight of the composition absent the temperature sensitive agent. A particularly preferred biocompatible plasticizer for use in the compositions described herein is dioctylphthalate or tributyl acetyl citrate.

Additionally, the cyanoacrylate compositions described herein preferably include a polymerization inhibitor in an effective amount to inhibit premature polymerization of the composition. In a particularly preferred embodiment, this inhibitor is sulfur dioxide which is employed at from about 50 to 500 ppm, more preferably from 200 to 500 ppm, based on the total weight of the composition absent the temperature sensitive indicator. Another preferred inhibitor is 4-methoxyphenol which is employed in an amount effective to inhibit premature polymerization. When employed, the amount of 4-methoxyphenol is preferably from about 50 to about 2500 ppm and more preferably about 250 ppm. Yet another preferred inhibitor is glacial acetic acid which is employed in an amount effective to inhibit premature polymerization.

The cyanoacrylate compositions may additionally contain one or more optional additives such as colorants, perfumes, rubber modifiers, modifying agents, etc. In practice, each of these optional additives should be both miscible and compatible with the cyanoacrylate composition and the resulting polymer. Compatible additives are those that do not prevent the use of the cyanoacrylates in the manner described herein.

Additionally, these compositions may further comprise an antimicrobial agent in an antimicrobially effective amount particularly when employed adjacent or over a skin wound such as a surgical site, a cut or scrap, or adjacent a decubitis ulcer. Suitable antimicrobial agents for use in cyanoacrylate compositions are disclosed by Greff, et al.[11] and Greff, et al.[12]

In general, colorants are preferably added so that the polymer layer formed on the skin will exhibit both enhanced color contrast and high color intensity. In order to improve color contrast, the liquid crystal compositions are preferably applied to and viewed against an absorptive, particularly a black background, which serves to absorb the transmitted light. In an alternative preferred embodiment, it is contemplated that absorptive, generally black particulate material is admixed with the liquid crystals, so as to absorb the transmitted light while not interfering excessively with the intensity of the scattered light. As an additional preferred alternative, it is contemplated that two or more dyes may be dissolved in the composition in a total dye concentration, each of the dyes reflecting light of a different wave length in the range of 400 to 700 nanometers, and the dyes together absorbing light of substantially all wave lengths within such range. Preferred dyes are disclosed in U.S. Pat. No. 4,015,591.[13]

In yet another alternative preferred embodiment, it is contemplated that the color background on mammalian skin can be applied in a separate layer to form a colored layer on the skin and then the prepolymer composition comprising the temperature indicator is applied over this colored layer in order to monitor the underlying skin temperature.

Perfumes are added to provide a pleasant smell to the formulation. Rubber modifiers are added to further enhance the flexibility of the resulting polymer layer. The amount of each of these optional additives employed in the composition is an amount necessary to achieve the desired effect.

Still further, it is contemplated that the cyanoacrylate composition can optionally comprise an acrylic monomer that will act as a polymeric plasticizer when it copolymerizes with the cyanoacrylate composition.

Utility

The methods described herein are useful in forming in situ a polymeric film on the skin surface of a mammalian patient which allows monitoring the temperature on the skin surface of a mammal. Such mammalian patients preferably include humans as well as, for example, domestic animals such as horses, cows, dogs, sheep, cats, etc.

The polymeric cyanoacrylate film of this invention finds particular utility in monitoring the skin surface temperature profile of a mammalian patient relative to the presence or absence of incipient diseases and disorders such as decreased circulation (e.g., incipient diabetic ulceration due to diabetes), solid mass tumors, basal cell carcinomas, sub-dermal infections (e.g., arising by infection of small wounds), inflammatory responses, and fevers as well as to monitor the condition of skin (e.g., in skin grafts, tissue flaps, frost-bite).

For example, in diabetes, diabetic ulcers are formed by deprivation of nutrients to the surface skin as a result of the diabetic condition including neuropathy, poor circulation in the patient, etc. In particular, diabetic ulcer formation in nutrient deprived surface skin areas is facilitated by skin irritation due to moisture, friction, and shearing forces. Typically, diabetic ulcer formation is preceded by reddening of nutrient deprived skin accompanied by a corresponding increase in skin temperature relative to adjacent unaffected skin. Monitoring this temperature differential will indicate incipient formation of a diabetic ulcer and permit the physician to aggressively treat this ulcer at an early stage before complications arise.

Decubitus ulcers, or bed sores, arise from the deprivation of nutrients to the tissue arising from prolonged pressure which leads to ischemia and are common in situations where the patient remains in a fixed position for prolonged periods (e.g., long term bed or wheelchair confinement). Typically, decubitus ulcer formation is preceded by reddening of nutrient deprived skin accompanied by a corresponding increase in skin temperature relative to adjacent unaffected skin. Monitoring this temperature differential will indicate incipient formation of a decubitus ulcer and permit the physician to aggressively treat this ulcer at an early stage before complications arise.

Differentials in temperature may also occur under normal conditions. Thus, the polymeric cyanoacrylate film also finds particular utility in detecting temperature phenomena of the healthy body such as, for example, vein location during venipuncture, or any other metabolic condition wherein there exists a temperature variation between the surrounding tissues and the area of interest. For example, certain individuals do not have easily located veins for blood withdrawal, catheter insertion or the like. The present cyanoacrylate composition may be applied over a region to determine the optimal position for venipuncture. The temperature sensitive indicator allows detection of otherwise undetectable veins. Once again, the composition may optionally comprise an antimicrobial agent to help inhibit infection. Application of the inventive composition helps prevent skin tearing adjacent the site of a catheter insertion.

These compositions may also be used in veterinary medicine to monitor the skin temperature around wounds on animals such as horses, dogs, pigs, cows, cats and the like which are prone to infection. The cyanoacrylate composition may be applied to monitor the temperature of the skin adjacent the wound as an indication of infection developing at the wound site. Again, the temperature sensitive agent allows early detection of wound infection as evidenced by an increase in temperature adjacent the wound as compared to surrounding tissues. Optionally, the cyanoacrylate composition will comprise an antimicrobial agent to help inhibit infection.

When used to monitor temperature in a mammal, the polymeric film will only adhere to the skin for a period of about 1–4 days after which time it sloughs off. This occurs because the cyanoacrylate polymer adheres only to the uppermost portion of the epidermal layer which is continuously in the process of being sloughed off and replaced by the underlying cells. Accordingly, the cyanoacrylate film need not be removed after in situ formation. However, if removal of the polymeric film is required, such can be accomplished with a solvent such as acetone (nail polish remover).

Kits

In view of the many different uses for topical application onto mammalian skin, this invention also encompasses a kit of parts useful for applying the cyanoacrylate compositions described herein onto mammalian skin. In particular, such a kit of parts comprises (a) a container comprising therein a prepolymeric composition as described above and (b) an applicator means for applying the composition onto mammalian skin.

In another of its kit aspects, this invention is also directed to kits useful for applying the cyanoacrylate compositions described herein onto mammalian skin. In particular, such a kit of parts comprises (a) a container comprising therein a polymerizable cyanoacrylate ester; (b) a container comprising an encapsulated temperature-sensitive indicator; and (c) an applicator means for applying the composition onto mammalian skin.

The container comprises any compatible material which stores the cyanoacrylate composition without degradation of the container or prematurely polymerizing the cyanoacrylate prepolymer. Such materials include, by way of example, inorganic materials such as Type 1 glass (including amber glass), ceramics, metals (e.g., aluminum, tin and tin coated tubes), etc. and organic materials such as inert polymers including polyolefins (e.g., high density polyethylene), fluorinated polyolefins, and the like. Examples of suitable containers include those recited in Bolduc, U.S. Pat. No. 5,154,320, which is incorporated herein by reference in its entirety.

Suitable applicator means include brushes, rollers, aerosols, swabs, foams (e.g., polyethylene foam) and the like. A particularly preferred applicator is described in U.S Pat. No. 4,183,684.[6]

In one embodiment, the container and applicator means are combined into a single article such as a brush affixed to the terminal portion of the container wherein means are employed to prevent premature release of the cyanoacrylate prepolymeric composition. For example, the brush may be overlaid with a removable impermeable barrier. When application of the cyanoacrylate prepolymer composition is intended, the barrier is simply removed.

In another embodiment, the container and applicator means are separate articles designed to mate with each other. For example, the cyanoacrylate prepolymer composition could be stored in a vial sealed with a screw cap and the applicator means includes a screw mechanism which mates with the screw mechanism on the top of the vial. When application of the cyanoacrylate prepolymer composition is intended, the cap is removed from the vial and the applicator is attached. The particular container/applicator means are not critical and there are numerous examples of such containers/applicators including those set forth by Bolduc[5], Lee, et al.[21], and Askill, et al.[22]

The following examples illustrate certain embodiments of the invention but are not meant to limit the scope of the claims in any way.

EXAMPLES

In the examples below, all temperatures are in degrees Celsius (unless otherwise indicated) and all percents are weight percent (also unless otherwise indicated). Additionally, the following abbreviations have the following meanings. If an abbreviation is not defined, it has its generally accepted meaning.

cm = centimeter
g = gram
min. = minutes
mL = milliliters
ppm = parts per million Example 1

This example illustrates how the composition of this invention can be prepared.

A composition of this invention is prepared by admixing 100 g of n-butyl cyanoacrylate, 20 g of tri(n-butyl) acetyl citrate (available from Aldrich Chemical Company, Milwaukee, Wis., USA), 150 ppm sulfur dioxide and 25 g of the encapsulated thermal indicator prepared as described below. The resulting admixture is stirred to homogeneity to provide for a cyanoacrylate prepolymer composition suitable for monitoring mammalian skin temperature.

The encapsulated thermal indicator is prepared from black backing temperature sensitive paint available from Cole-Parmer Instrument Company as Catalog number E-90320-35 (30° C. to 35° C.) or E-90320-40 (35° C. to 40° C.). Specifically, 250 mL of this paint is centrifuged to recover a solid mass which comprises the thermal indicator. This mass can optionally be further purified by conventional techniques such as filtration, liquid-liquid extraction and the like.

Alternatively, compositions comprising encapsulated temperature sensitive indicators can be obtained commercially from Hallcrest, Inc., Glenview, Ill., USA which compositions can be used in Example 1 above to prepare cyanoacrylate compositions comprising such indicators.

Examples 2 and 3 as follows illustrate how the cyanoacrylate prepolymeric compositions of this invention can be used to form a polymeric film on mammalian skin to monitor skin temperature.

Example 2

During a routine examination by a physician of a 67 year old female with refractory diabetes and peripheral neuropathy due to her diabetes, a reddened area around the top inner portion of her left foot is noticed. Since the patient has reduced sensation, she is at risk of skin/tissue damage most likely caused by improperly matched gait/footwear. Once compromised, damaged diabetic skin heals poorly.

To address this problem, about 6 to 10 drops of the formulation of Example 1 is applied evenly to the reddened surface area and additionally about 3 to 5 cm beyond with a finger tip by a care giver. A flexible, smooth, surface conforming coating forms within about 1 min. This process is repeated every other day for about two weeks to replace the coating normally shed with the skin, being careful to avoid a build up or a thick coating.

The care giver examines the treated foot twice a day noting temperature differentials on the foot as evidenced by the temperature sensitive indicator and correlates these temperature differentials with incipient tissue damage. With this information, a physician prescribes custom designed footwear and padding to prevent tissue damage and ulceration at this site.

Example 3

A 44 year old male is hospitalized with a fresh skin flap autograft (4×6 cm) sutured onto his left hip. The autograft may "take" and become vascularized or fail and necrose.

Since successful autografts are characterized by a higher skin temperature than failed autografts, the progress of the autograft is monitored by applying the composition of Example 1 to the autograft and additionally to about 3 to 7 cm beyond. About 8 to 12 drops of the formulation is applied evenly to the surface with a finger tip by the nurse or physician. A flexible, smooth, surface conforming coating forms within about 3 min. This process is repeated every other day for about 10 days to replace the coating normally shed with the skin, being careful to avoid a build up or a thick coating. The nurse or physician examines the treated area three times a day noting the specific temperature profile of the autograft as an indication of acceptance or failure of the autograft. On day 5, upon finding the indicator color in the film on the autograft and the surrounding tissue to be similar, autograft acceptance is confirmed.

What is claimed is:

1. A cyanoacrylate composition which comprises:
   (a) a polymerizable cyanoacrylate ester which is a polymerizable monomer or oligomer of a cyanoacrylate ester which, in monomeric form, is represented by formula I:

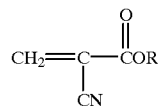

wherein R is selected from the group consisting of alkyl, alkenyl, cycloalkyl, aryl, alkalkoxy, and a substituent of the formula:

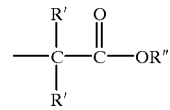

wherein each R' is independently selected from the group consisting of hydrogen and methyl, and R" is selected from the group consisting of alkyl, alkenyl, alkynyl, cycloalkyl, aralkyl, aryl, and substituted aryl; and
   (b) an effective amount of an encapsulated temperature-sensitive indicator.

2. The cyanoacrylate composition according to claim 1 wherein R is alkyl of from 2 to 10 carbon atoms.

3. The cyanoacrylate composition according to claim 2 wherein R is alkyl of from 4 to 10 carbon atoms.

4. The cyanoacrylate composition according to claim 3 wherein R is selected from the group consisting of butyl, octyl or decyl.

5. The cyanoacrylate composition according to claim 4 wherein R is n-butyl.

6. The cyanoacrylate composition according to claim 1 wherein said encapsulated temperature-sensitive material emits a unique signal corresponding to a specific temperature.

7. The cyanoacrylate composition according to claim 6 wherein the encapsulated temperature sensitive material is selected from the group consisting of enantiotropic cholesteric liquid crystalline phase materials or liquid crystals.

8. The cyanoacrylate composition according to claim 1 wherein said encapsulated temperature sensitive material is selected from the group consisting of: cholesterol erucyl carbonate, cholesterol methyl carbonate, cholesterol oleyl carbonate, cholesterol para-nonyl phenyl carbonate, cholesterol phenyl carbonate, cholesterol acetate, cholesterol benzoate, cholesterol butyrate, cholesterol isobutyrate, cholesterol chloride, cholesterol chloroacetate, cholesterol cinnamate, cholesterol crotanoate, cholesterol decanoate, cholesterol erucate, cholesterol heptanoate, cholesterol hexanoate, cholesterol myristate, cholesterol nonanoate, cholesterol octanoate, cholesterol oleate, cholesterol propionate, cholesterol valerate, dichloresteryl carbonate, cholestanyl benzoate, sitosteryl nonanoate and mixtures thereof.

9. The cyanoacrylate composition according to claim 1 which further comprises a biocompatible plasticizer.

10. The cyanoacrylate composition according to claim 1 which further comprises an antimicrobial agent.

11. A cyanoacrylate composition which comprises:

(a) a polymerizable cyanoacrylate ester which, in monomeric form, is represented by formula II:

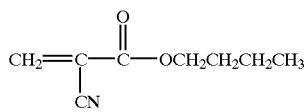

II (b) an effective amount of a composition comprising a cholesteric mesophase in order to monitor mammalian skin temperatures.

12. The cyanoacrylate composition according to claim 11 wherein said cholesteric mesophase is formed from a mixture of two or more components selected from the group consisting of cholesterol erucyl carbonate, cholesterol methyl carbonate, cholesterol oleyl carbonate, cholesterol para-nonyl phenyl carbonate, cholesterol phenyl carbonate, cholesterol acetate, cholesterol benzoate, cholesterol butyrate, cholesterol isobutyrate, cholesterol chloride, cholesterol chloroacetate, cholesterol cinnamate, cholesterol crotanoate, cholesterol decanoate, cholesterol erucate, cholesterol heptanoate, cholesterol hexanoate, cholesterol myristate, cholesterol nonanoate, cholesterol octanoate, cholesterol oleate, cholesterol propionate, cholesterol valerate, dichloresteryl carbonate, cholestanyl benzoate and sitosteryl nonanoate.

13. A method of monitoring the surface skin temperature of a mammal which method comprises:

applying to at least a portion of the skin surface of said mammal a sufficient amount of a cyanoacrylate composition which comprises a polymerizable cyanoacrylate ester and an effective amount of an encapsulated temperature-sensitive indicator which provides a unique signal corresponding to a specific temperature of the skin surface;

polymerizing the cyanoacrylate composition so as to form a polymeric film which adheres to the surface where the composition was applied; and monitoring the temperature of said mammal by correlating the unique signal emitted by the temperature-sensitive indicator to the particular temperature to which it corresponds.

14. The method according to claim 13 wherein the polymerizable cyanoacrylate ester is a polymerizable monomer or oligomer of a cyanoacrylate ester which, in monomeric form, is represented by formula I:

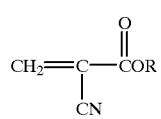

I wherein R is selected from the group consisting of alkyl, alkenyl, cycloalkyl, aryl, alkalkoxy, and a substituent of the formula:

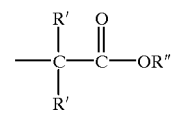

wherein each R' is independently selected from the group consisting of: hydrogen and methyl, and R" is selected from the group consisting of: alkyl, alkenyl, alkynyl, cycloalkyl, aralkyl, aryl, and substituted aryl.

15. The method according to claim 14 wherein R is alkyl of from 2 to 10 carbon atoms.

16. The method according to claim 15 wherein R is alkyl of from 4 to 10 carbon atoms.

17. The method according to claim 16 wherein R is selected from the group consisting of butyl, octyl or decyl.

18. The method according to claim 17 wherein R is n-butyl.

19. The method according to claim 13 wherein said encapsulated temperature-sensitive material emits a unique colored signal corresponding to a specific temperature of the skin surface.

20. The method according to claim 19 wherein said encapsulated temperature sensitive material is selected from the group consisting of enantiotropic cholesteric liquid crystalline phase materials or liquid crystals.

21. The method according to claim 19 wherein said encapsulated temperature sensitive material is selected from the group consisting of: cholesterol erucyl carbonate, cholesterol methyl carbonate, cholesterol oleyl carbonate, cholesterol para-nonyl phenyl carbonate, cholesterol phenyl carbonate, cholesterol acetate, cholesterol benzoate, cholesterol butyrate, cholesterol isobutyrate, cholesterol chloride, cholesterol chloroacetate, cholesterol cinnamate, cholesterol crotanoate, cholesterol decanoate, cholesterol erucate, cholesterol heptanoate, cholesterol hexanoate, cholesterol myristate, cholesterol nonanoate, cholesterol octanoate, cholesterol oleate, cholesterol propionate, cholesterol valerate, dichloresteryl carbonate, cholestanyl benzoate, sitosteryl nonanoate and mixtures thereof.

22. The method according to claim 13 which further comprises a biocompatible plasticizer.

23. The method according to claim 13 which further comprises an antimicrobial agent.

24. A method of monitoring the surface skin temperature of a mammal which method comprises:

applying to at least a portion of the skin surface of said mammal a sufficient amount of a cyanoacrylate composition which comprises a polymerizable cyanoacrylate ester and an effective amount of an encapsulated temperature-sensitive indicator which provides a unique signal corresponding to a specific temperature of the skin surface wherein the polymerizable cyanoacrylate ester, in monomeric form, is represented by formula II:

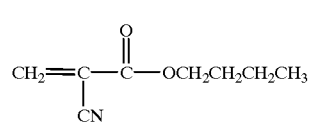

II and further wherein said encapsulated temperature-sensitive indicator comprises an encapsulated cholesteric mesophase.

25. The method according to claim 24 wherein said cholesteric mesophase is formed from a mixture of two or more components selected from the group consisting of cholesterol erucyl carbonate, cholesterol methyl carbonate, cholesterol oleyl carbonate, cholesterol para-nonyl phenyl carbonate, cholesterol phenyl carbonate, cholesterol acetate, cholesterol benzoate, cholesterol butyrate, cholesterol isobutyrate, cholesterol chloride, cholesterol chloroacetate, cholesterol cinnamate, cholesterol crotanoate, cholesterol decanoate, cholesterol erucate, cholesterol heptanoate, cholesterol hexanoate, cholesterol myristate, cholesterol nonanoate, cholesterol octanoate, cholesterol oleate, cholesterol propionate, cholesterol valerate, dichloresteryl carbonate, cholestanyl benzoate and sitosteryl nonanoate.

26. A method of determining a temperature differential on adjacent skin surfaces of a mammal which comprises:
applying to said adjacent skin surfaces of said mammal a sufficient amount of a cyanoacrylate composition comprising a polymerizable cyanoacrylate ester and an effective amount of an encapsulated temperature-sensitive indicator which provides a unique signal corresponding to a specific temperature of the skin surface;
polymerizing the cyanoacrylate composition so as to form a polymeric film which adheres to the area where the composition was applied; and
determining any temperature differentials between the adjacent skin surfaces by monitoring the signals emitted by the temperature-sensitive indicator on said adjacent skin surfaces.

27. The method according to claim 26 wherein the polymerizable cyanoacrylate ester is a polymerizable monomer or oligomer of a cyanoacrylate ester which, in monomeric form, is represented by formula I:

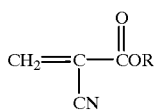

wherein R is selected from the group consisting of alkyl, alkenyl, cycloalkyl, aryl, alkalkoxy, and a substituent of the formula:

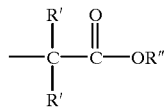

wherein each R' is independently selected from the group consisting of: hydrogen and methyl, and R" is selected from the group consisting of: alkyl, alkenyl, alkynyl, cycloalkyl, aralkyl, aryl, and substituted aryl.

28. The method according to claim 27 wherein R is alkyl of from 2 to 10 carbon atoms.

29. The method according to claim 28 wherein R is alkyl of from 4 to 10 carbon atoms.

30. The method according to claim 29 wherein R is selected from the group consisting of butyl, octyl or decyl.

31. The method according to claim 30 wherein R is n-butyl.

32. The method according to claim 26 wherein said encapsulated temperature-sensitive material emits a unique colored signal corresponding to a specific temperature of the skin surface.

33. The method according to claim 32 wherein said encapsulated temperature sensitive material is selected from the group consisting of enantiotropic cholesteric liquid crystalline phase materials or liquid crystals.

34. The method according to claim 32 wherein said encapsulated temperature sensitive material is selected from the group consisting of: cholesterol erucyl carbonate, cholesterol methyl carbonate, cholesterol oleyl carbonate, cholesterol para-nonyl phenyl carbonate, cholesterol phenyl carbonate, cholesterol acetate, cholesterol benzoate, cholesterol butyrate, cholesterol isobutyrate, cholesterol chloride, cholesterol chloroacetate, cholesterol cinnamate, cholesterol crotanoate, cholesterol decanoate, cholesterol erucate, cholesterol heptanoate, cholesterol hexanoate, cholesterol myristate, cholesterol nonanoate, cholesterol octanoate, cholesterol oleate, cholesterol propionate, cholesterol valerate, dichloresteryl carbonate, cholestanyl benzoate, sitosteryl nonanoate and mixtures thereof.

35. The method according to claim 26 which further comprises a biocompatible plasticizer.

36. The method according to claim 26 which further comprises an antimicrobial agent.

37. The method according to claim 26 wherein the temperature differential on adjacent surfaces of mammalian skin corresponds to a disease condition in the mammal.

38. The method according to claim 37 wherein the disease condition is selected from the group consisting of diabetic ulceration, decubitis ulceration, solid mass tumors, subdermal infections, inflammatory responses, and fevers.

39. The method according to claim 26 wherein the temperature differential on adjacent surfaces of mammalian skin corresponds to placental location during pregnancy and vein location during venipuncture.

40. A kit of parts comprising
(a) a container comprising therein:
(i) a polymerizable cyanoacrylate ester; and
(ii) an effective amount of an encapsulated temperature-sensitive indicator; and
(b) an applicator means for applying the composition onto mammalian skin.

41. A kit of parts according to claim 40 wherein the container and applicator means are combined into a single article.

42. A kit of parts according to claim 41 wherein the container and applicator means are separate articles.

43. A kit of parts comprising:
(a) a container comprising therein a polymerizable cyanoacrylate ester;
(b) a container comprising an encapsulated temperature-sensitive indicator; and
(c) an applicator means for applying the composition onto mammalian skin.

* * * * *